(12) United States Patent
Pfeil et al.

(10) Patent No.: US 10,448,974 B2
(45) Date of Patent: Oct. 22, 2019

(54) FLEXIBLE IMPLANT FOR DISTRACTION

(71) Applicant: KYON AG, Zurich (CH)

(72) Inventors: Ingo Michael Pfeil, Langebruck (DE); Slobodan Tepic, Zurich (CH)

(73) Assignee: Kyon AG, Zurich (CH)

( * ) Notice: Subject to any disclaimer, the term of this patent is extended or adjusted under 35 U.S.C. 154(b) by 196 days.

(21) Appl. No.: 15/306,213

(22) PCT Filed: Apr. 27, 2015

(86) PCT No.: PCT/IB2015/001166
§ 371 (c)(1),
(2) Date: Oct. 24, 2016

(87) PCT Pub. No.: WO2015/162496
PCT Pub. Date: Oct. 29, 2015

(65) Prior Publication Data
US 2017/0042582 A1    Feb. 16, 2017

Related U.S. Application Data

(60) Provisional application No. 61/984,383, filed on Apr. 25, 2014.

(51) Int. Cl.
*A61B 17/70* (2006.01)
*A61B 17/02* (2006.01)
(Continued)

(52) U.S. Cl.
CPC ............ *A61B 17/70* (2013.01); *A61B 17/025* (2013.01); *A61B 17/7059* (2013.01);
(Continued)

(58) Field of Classification Search
CPC .... A61B 17/7002–7031; A61B 17/025; A61B 17/60; A61B 17/66; A61B 2017/681; A61B 17/0256
See application file for complete search history.

(56) References Cited

U.S. PATENT DOCUMENTS 2,580,821 A    1/1952  Toufick
4,422,451 A *  12/1983 Kalamchi .......... A61B 17/7002
                                           606/207

(Continued)

FOREIGN PATENT DOCUMENTS

WO    2005/074825     8/2005
WO    WO2005/074825   8/2005

*Primary Examiner* — Nicholas J Plionis
(74) *Attorney, Agent, or Firm* — Occhiuti & Rohlicek LLP (57) ABSTRACT

Disclosed herein are distraction implants for treating, for example, spinal disorders. The implants can be comprised of a U-shaped elastic member, two bone anchor members and two tension members to couple the components together. Use of the tension members allows for transfer of distraction force without unintended forces in the perpendicular plane and parasitic moments. As there are several options for anchoring to bone, the present implants can be applied to all segments of the spine from the cervical spine to the lumbar regions. The implant can be temporary or permanent, covering indications from fracture treatment to management of chronic disc disorders, including disc protrusion. Use of the present implant and methods of use are also within the scope of the invention.

17 Claims, 7 Drawing Sheets

(51) Int. Cl.
    *A61B 17/00* (2006.01)
    *A61B 17/56* (2006.01)
    *A61B 17/68* (2006.01)

(52) U.S. Cl.
    CPC .............. *A61B 2017/00862* (2013.01); *A61B 2017/0256* (2013.01); *A61B 2017/567* (2013.01); *A61B 2017/681* (2013.01)

(56) References Cited

U.S. PATENT DOCUMENTS

| | | | |
|---|---|---|---|
| 4,870,957 A | | 10/1989 | Goble et al. |
| 9,155,569 B2 | * | 10/2015 | Konieczynski .... A61B 17/7071 |
| 10,143,498 B2 | * | 12/2018 | Roger ................ A61B 17/7032 |
| 2005/0171539 A1 | * | 8/2005 | Braun ................ A61B 17/7059 |
| | | | 606/279 |
| 2006/0240533 A1 | | 10/2006 | Sengupta et al. |
| 2006/0264948 A1 | * | 11/2006 | Williams .............. A61B 17/70 |
| | | | 606/71 |
| 2008/0188856 A1 | | 8/2008 | Casutt |
| 2009/0088799 A1 | * | 4/2009 | Yeh .................... A61B 17/7005 |
| | | | 606/246 |
| 2009/0105822 A1 | * | 4/2009 | Ogilvie ................ A61B 17/56 |
| | | | 623/17.11 |
| 2009/0234388 A1 | * | 9/2009 | Patterson ............ A61B 17/702 |
| | | | 606/246 |

* cited by examiner

FLEXIBLE IMPLANT FOR DISTRACTION

CROSS REFERENCE TO RELATED APPLICATION

This application is a U.S. national phase application, filed under 35 U.S.C. § 371, of International Application No. PCT/IB2015/001166, filed Apr. 27, 2015, which claims the benefit of the filing date of U.S. Provisional Application No. 61/984,383, filed Apr. 25, 2014. The content of U.S. Provisional Application No. 61/984,383 is hereby incorporated by reference herein in its entirety.

FIELD OF THE INVENTION

The invention relates to implants and methods for treating a spine or another skeletal structure in need of flexible distraction.

BACKGROUND OF THE INVENTION

The spinal column is prone to disc injuries that are usually chronic in nature, but which can frequently culminate in disc protrusions, or extrusions, with potentially serious neurological consequences, including paralysis. Traumatic compression fractures of the vertebral bodies are also frequently seen and difficult to treat with the conventional means for fracture fixation of long bones. When used, plates and screws, for example, inevitably lead to bony fusion over one or more of the spinal discs because several vertebral bodies on each side of the fractured body must be used for fixation to get sufficient mechanical grip. There are numerous other specialized devices for these indications, but they all tend to involve a plurality of spinal column elements.

There are many different devices for treating disc extrusions, including fusion cages and disc prostheses. These devices are associated with high morbidity and require costly, complex surgical procedures.

Disc injuries are prevalent in both human patients and veterinary fields, although usually for somewhat different reasons.

SUMMARY OF THE INVENTION

This invention provides devices and methods that provide for a less invasive yet more robust stabilization of defective skeletal bodies (e.g., spinal column segments). The device comprises: (i) an elastic member; (ii) two anchor members for transferring distraction force to the spinal column utilizing bone screws; and (iii) two flexible tension members for connecting the elastic member to the anchor members.

Flexibility of the tension member(s) allows application of a distraction force to the anchor member(s) without a coupled bending or torsion moment. This is important since it greatly reduces the stresses on the device/bone interface while also allowing some movement between the points of anchorage in all other degrees of freedom.

All components of the device can be manufactured from metal, preferably from a titanium alloy with high strength, low modulus of elasticity and superb biocompatibility.

The tension members can also be manufactured using non-metallic materials such as high strength polymeric fibers and in particular UHMWPE (ultra high molecular weight polyethylene) fibers.

For improved strength and reliability, one can use locking screws such as those described in Perren et al. (U.S. Pat. No. 5,053,03; see also U.S. Pat. No. 5,180,382) to couple the anchor members to the bones. In many cases, a single screw may suffice; in most cases, two screws will provide an increased margin of safety, anatomical space permitting. The bone screw can include a head end, a tip end, and a shaft extending between the head end and the tip end. The shaft has a first threaded segment toward the head end, with a minor diameter $d_1$ and a second threaded segment towards the tip end with a minor diameter $d_2$, $d_2$ being less than $d_1$, and the thread in said segments having the same pitch. In some embodiments, a third transition segment is provided between the first and second segments. The screw tip can be designed to be self-cutting (e.g., in the form of a trocar or one or more cutting grooves radially distributed over the circumference.

Accordingly, in a first aspect, the present invention features an implant for flexible distraction between two anchor points on the skeleton of a human or veterinary patient. More specifically, the implant comprises an elastic member, two anchor members, and two flexible tension members configured such that the elastic member straddles the two anchor members and applies a distraction force to the anchor members via the two flexible tension members situated between the elastic member and the two anchor members. The elastic member includes two terminal regions, with a flexible tension member connecting each terminal region to an anchor member. The implants in general and the component parts thereof (e.g., the two anchor member(s)) can be configured in size and shape for attachment to a spine of a human or veterinary patient. For example, the first anchor point can be located on a first vertebrae and the second anchor point can be located on a second (e.g., adjacent) vertebrae. The flexible tension member(s) can include a conical coupling element affixed (permanently or temporarily) to a flexible cable or bundle of filaments). The implant and component parts thereof (e.g., the flexible cable or bundle of filaments) can be or can include a titanium alloy (e.g., titanium-aluminium-vanadium, titanium-aluminium-niobium or a super-elastic nickel-titanium). The flexible cable or bundle of filaments can also, or alternatively, include high strength polymeric fibers (e.g., ultra high molecular weight polyethylene). In particular embodiments, the present implants can further include one or more (e.g., two) two bone screws (e.g., locking bone screws) for attaching the anchor member(s) to bone.

In another aspect, the invention features an implant for flexible distraction between two anchor points on the skeleton of a human or veterinary patient, with the implant comprising an elastic member having one terminal region that attaches to the anchor point by a conventional means (e.g., by a bone screw or nail, by a glue, cement, or like substance, or by a suture). The implant further comprises a terminal region configured as described above (i.e., configured to interact with the anchor member via a flexible tension member. Thus, the implant can include first and second terminal regions, an anchor member, and a flexible tension member, wherein the first terminal region comprises means for attaching the elastic member to a skeletal element by conventional mechanisms and the second terminal region interacts with the anchor member via the unique flexible tension member described herein. In this aspect, the implant can include a first terminal region comprising an opening configured to receive a bone anchor, a surface compatible with bone cement (e.g., a flat, roughened surface), or a feature that can be affixed with a surgical suture (e.g., an opening or eyelet).

In another aspect, the invention features methods of treating a patient who is suffering from an injury to the spine or a disease that causes damage to a spinal disc. The methods can include the step of affixing an implant described herein to vertebrae in the injured or diseased area of the spine. Other areas of the body in which distraction is indicated may also be treated. The injury to the spine can be a fracture, and in any event, the patient can be a human or a domesticated animal.

DETAILED DESCRIPTION

The present invention provides a fixation system for distraction between two anchor points on a skeleton of a human or veterinary patient. Most frequently this need arises in connection with the spine, either in disc pathologies or in fractures of the vertebral bodies. Accordingly, the methods of the invention encompass treating a patient having a disc pathology or a fracture of a vertebral body. In any embodiment, the methods can include a step of identifying a patient in need of treatment.

The defining feature of the system is its force controlling U-shaped spring, herein referred to as the elastic member. This elastic member straddles the two anchor members and applies tensile force to them via flexible tension members, essentially short segments of a cable provided with conical ends that engage conical recesses in the elastic member and in the anchor members. Thus, the elastic member can be U-shaped, flexible, dimensioned to straddle two anchor members, and designed to engage the flexible tension members at its free ends (i.e., the termination of the arms of the U).

The implants can be designed in a very broad range of sizes to accommodate a variety of anatomical structures and can be manufactured with varying stiffnesses controlled by the geometry and the material employed. The materials of choice for most of these components are titanium alloys, e.g. titanium-aluminium-vanadium or titanium-aluminium-niobium. However, various beta alloys of titanium, as well as super-elastic Nitinol® (nickeltitanium), can also be used.

Figure 1:
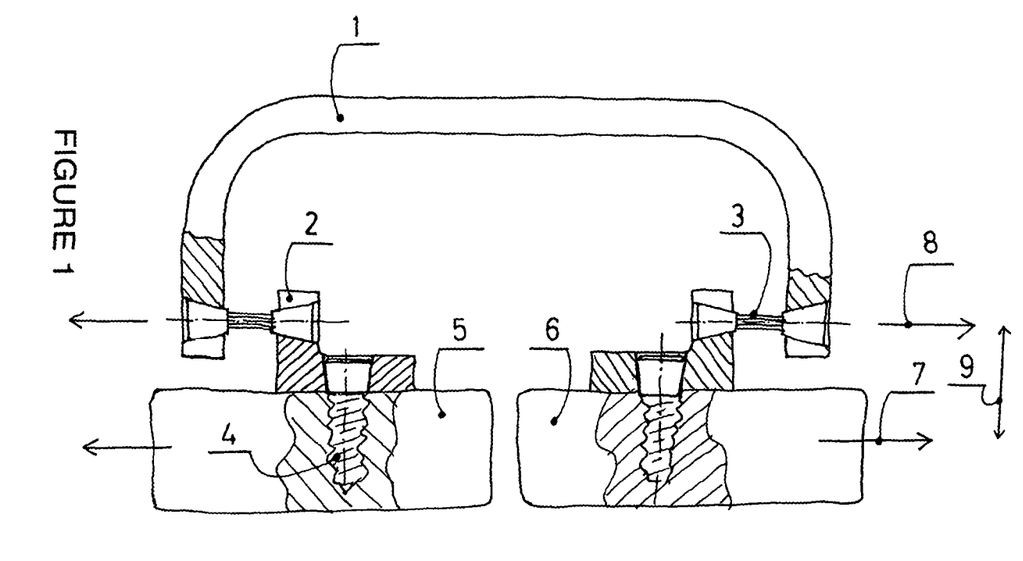
FIG. 1 is a side view of an implant according to the present invention.

FIG. 1 is a schematic representation of a device according to the present invention showing the elastic member 1 arching over two anchor members 2, affixed to the skeletal bodies 5 and 6 with screws 4. The elastic member 1 is connected to anchor members 2 via tension members 3. Called for distraction force 7 is generated by elastically deforming the member 1 and then coupling it to the anchor members 2 via tension members 3. The device produces distraction force 8 approximately of the same magnitude as 7, but offset by the distance 9. In most cases, the distance 9 should be kept to a minimum, but by strategic placement of the anchors members, or using them in pairs, the effects of the bending moment generated by the offset 9 can be minimized or put to good use. Flexibility of the tension members 3 allows transfer of the force 8 to the anchor members with only minimal forces in the other two directions or any of the three moments.

Figure 2:
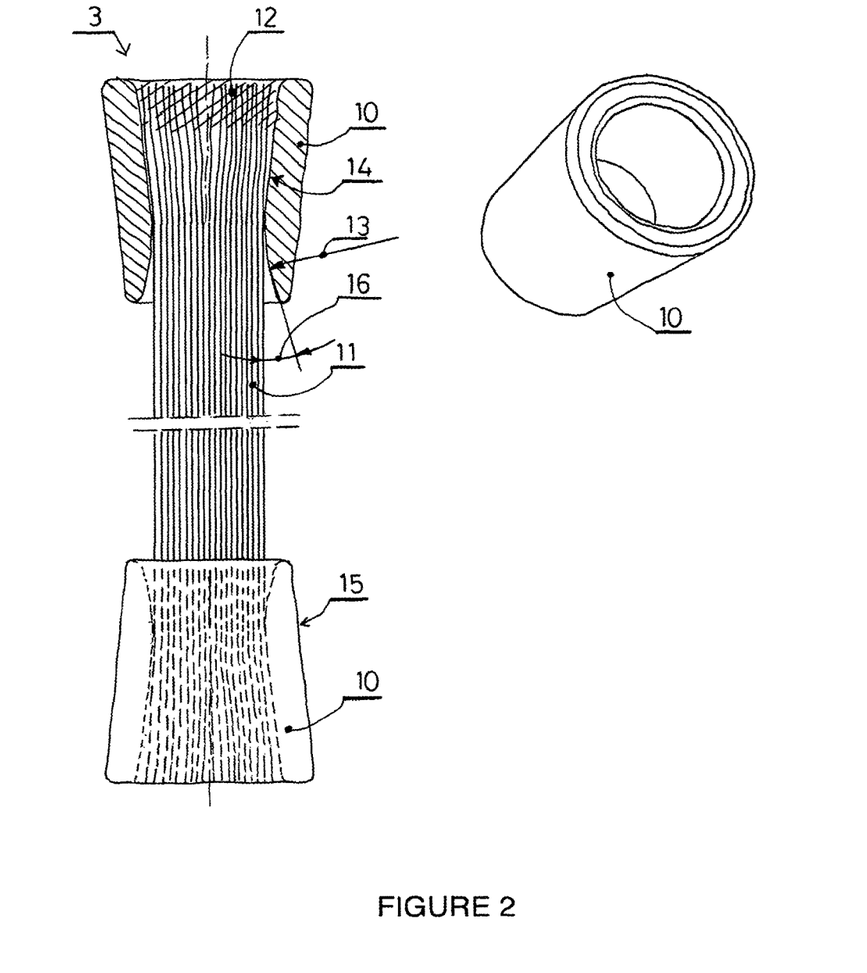
FIG. 2 is a partial cross-sectional view of the flexible tension member.

FIG. 2 shows the tension member 3 in a partial cross-section and the conical coupling element 10 in a perspective view. A bundle of fibers 11 is fixed within the coupling element 10, by welding or brazing 12, or other mechanical means if, for example, polymeric fibers are used in the bundle 11. The exit end of the coupling element 10 is conical in shape, as shown by arrow 14. Once the ends of the bundle 11 are welded, brazed or otherwise affixed to the element 10, the conical ends of the hole provide for higher resistance against the pullout of the bundle from the connecting element 10. Transition from the exit section of the element 10 to the entry section is formed with a radius of curvature 13, which provides the surface over which the fibers of the bundle 11 are bending. In preferred embodiments, the ratio of the radius of curvature 13 to the diameter of the individual fibers extending through the conical coupling element 10 should be maximized within technical limits. Tangential entry conical section allows the bundle to bend over the radius 13 by an angle 16 in each direction, without contacting the end face of the connecting element 10. The connecting element's outside shape can also be conical, as shown by the arrow 15, so that the connections to both the anchor member 2 (FIG. 1) and the elastic member 1 (FIG. 1) are strong and protected from fretting. The angle of this conical section can be as small as needed for self-locking, or somewhat larger to facilitate removal, if needed. The range considered best suited, expressed in the usual way of defining the conical section by the ratio of the change in the diameter to the length of the cone, is 1:10 (which leads to safe self-locking) to 1:5 (which does not result in self-locking, but provides secure contact conditions). The final choice is affected by the materials used and the surface finish of the interfaced components.

For optimal distribution of forces between the fibers in the bundle 11 when bending over the radius 13, there should preferably by a twist (e.g., of about 180 degrees) in the bundle over its length (not shown). By "about" we mean plus-or-minus 10%.

Figure 3:
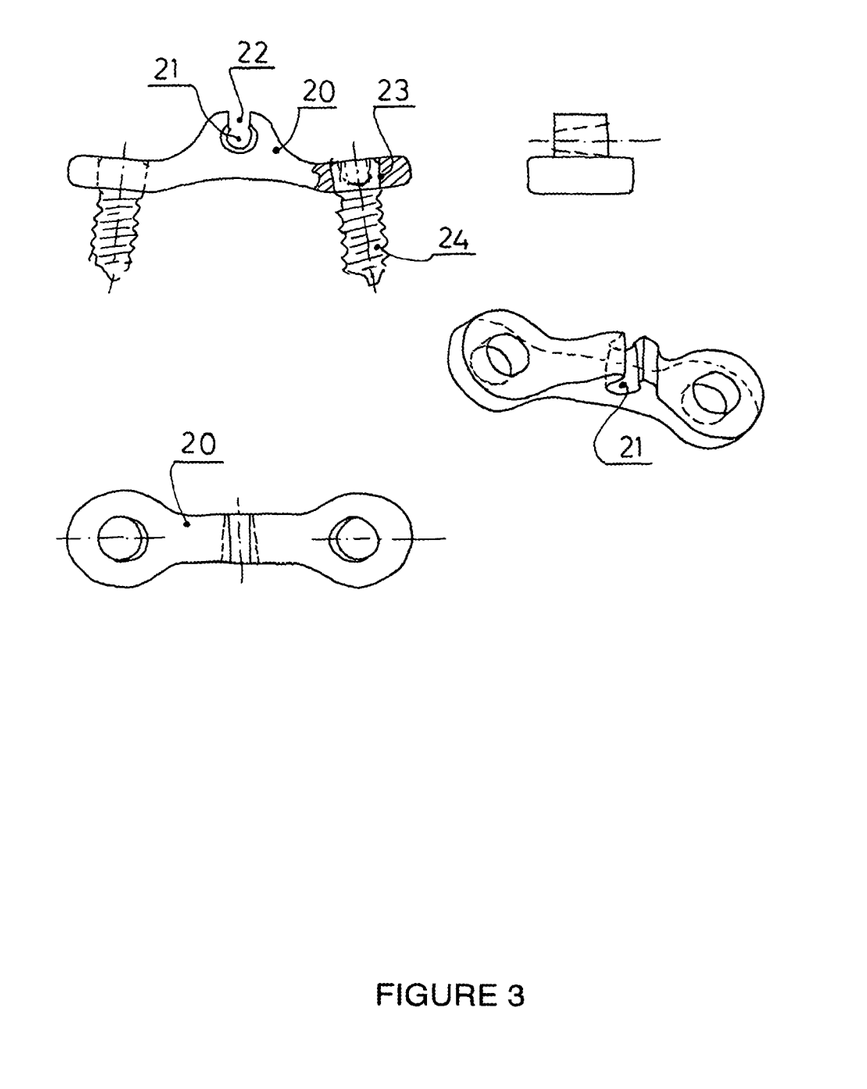
FIG. 3 shows orthogonal views and a perspective view of the anchor member with two screw-fixation and transverse groove for coupling with the flexible tension member.

FIG. 3 shows orthogonal views and a perspective view of the anchor member 20 provided with two holes 23 for insertion of the bone screws 24. The axes of the screws can be somewhat divergent, as shown here, for a safer insertion on the dorsal side of the spinal vertebra. The conical hole 21, oriented in the transverse direction to the axis of the member 20, is matched to receive the conical elements 10 of the tension member 3 (FIG. 2). The opening 22 into the hole 21, allows the bundle 11 (FIG. 2) to be slipped down into the hole 21, before pulling on the member 3 to get the element 10 to engage with hole 21.

Figure 4:
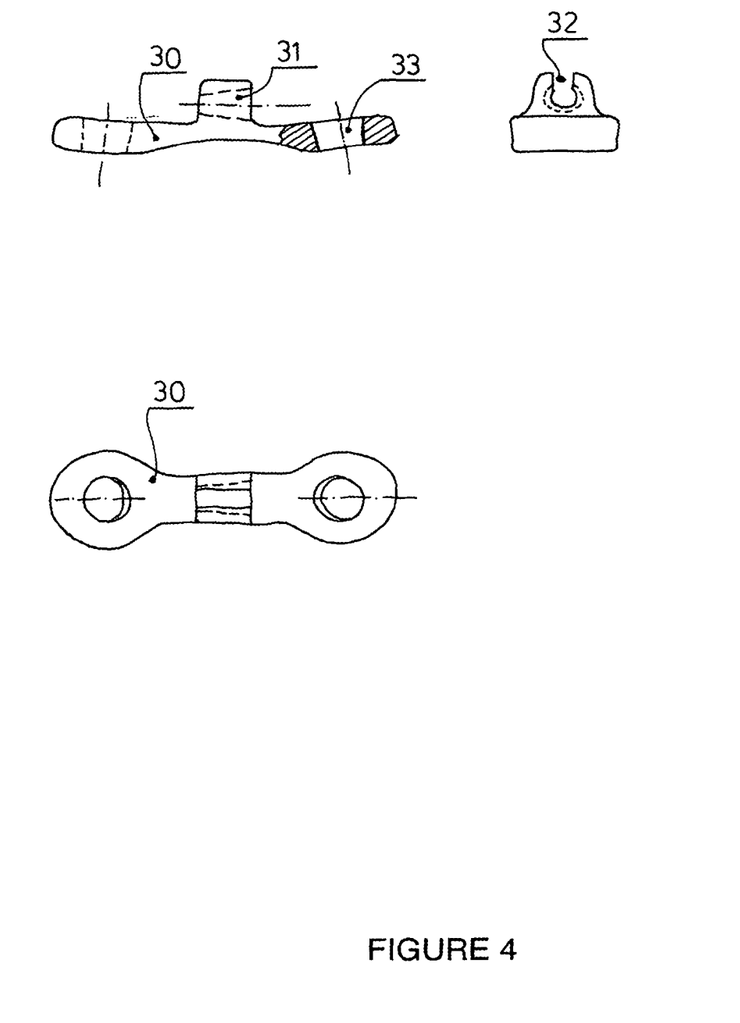
FIG. 4 shows orthogonal views of the anchor member with two screw-fixation and longitudinal groove for coupling with the flexible tension member.

FIG. 4 shows an alternative orientation of the receiving hole 31 in the anchor element 30. The axis of the hole 31 and the opening 32 is now along the long axis of 30, in line with the screw holes 33.

Figure 5:
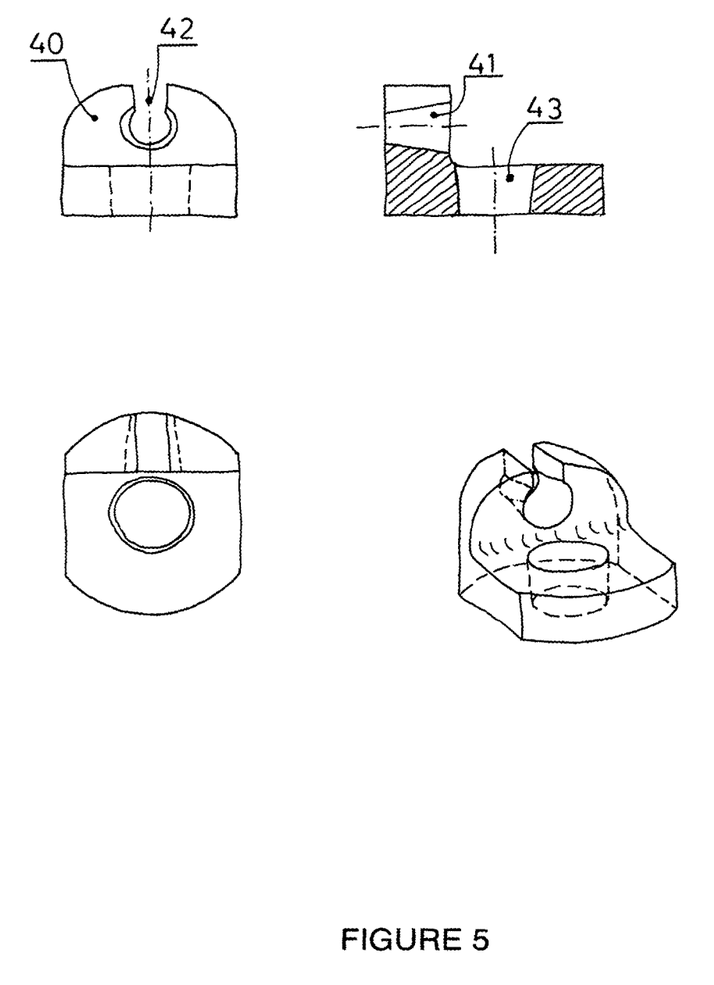
FIG. 5 shows orthogonal views and a perspective view of the anchor member with one screw-fixation.

FIG. 5 shows another embodiment 40 of the anchor member. Only one screw hole 43 is provided for fixation to the bone. The hole 41 for receiving the tension member is set above the screw hole, as close as possible. The opening 42 into the hole 41 is also shown here.

Figure 6:
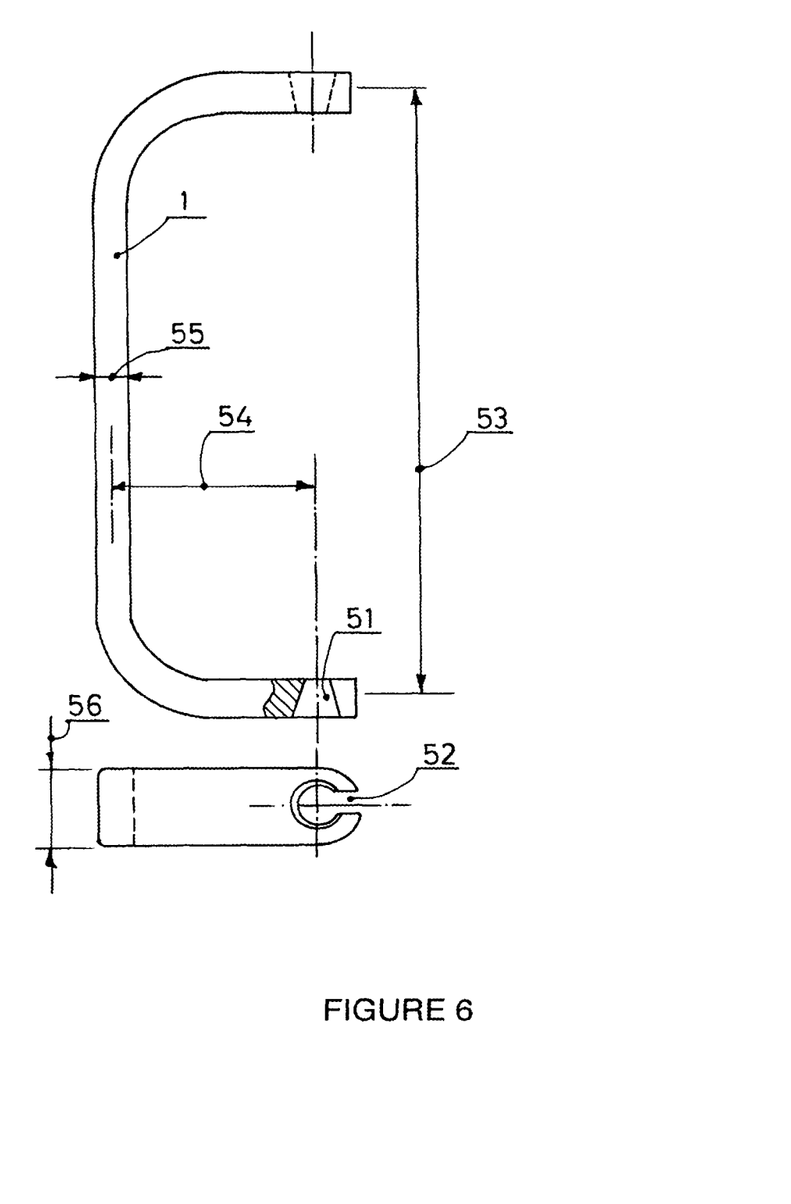
FIG. 6 shows orthogonal views of the elastic member.

FIG. 6 shows orthogonal views of the elastic member 1, generally U-shaped (with the base of the "U" being longer than the arms of the "U" in this illustrated embodiment).

Distance 54 from the receiving holes 51 for the tension members to the spine of the member 1, is one of the factors controlling the elasticity and strength of the device. The other defining parameters are the length 53 and the cross-sectional dimensions 55 (the width) and 56 (the thickness). A rectangular section has been chosen to facilitate production from a plate by cutting the U-shape. In general terms, the length 53 will be dictated by the anatomy of the location where the implant is being deployed. Anatomy also plays a major role in defining the limits on the height 54 of the device. A large range of desired mechanical properties can be achieved by choosing the width 55 and the thickness 56.

Figure 7:
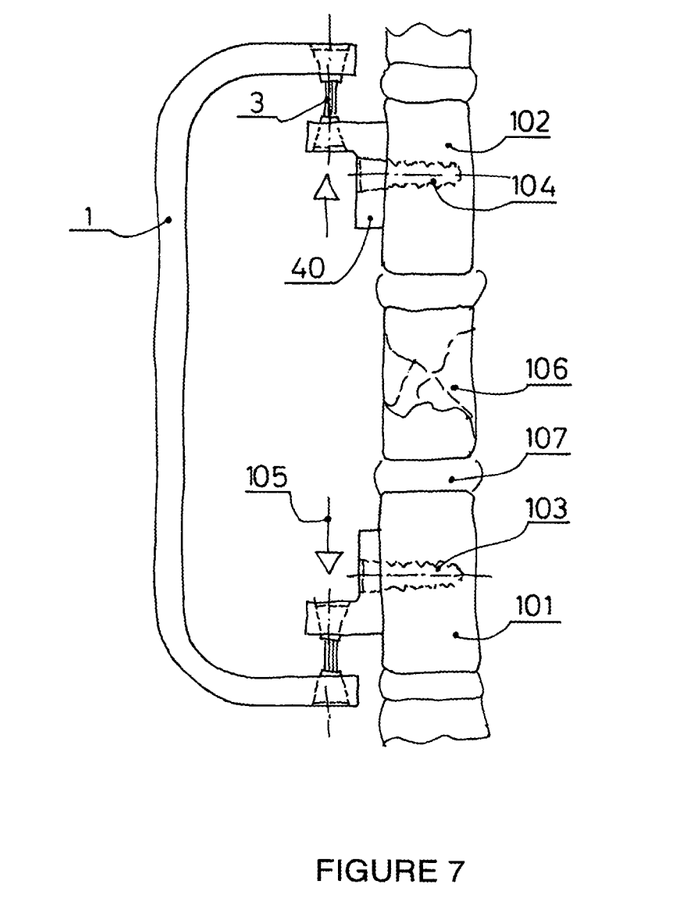
FIG. 7 shows the implant according to the invention applied to a spine that needs distraction.

FIG. 7 is a schematic representation of a device of the invention in use on the spinal column. A compression fracture 106 of a vertebral body can be treated by distracting the adjacent vertebral bodies 101 and 102 using the elastic member 1, coupled to them by bone screws 103 and 104, respectively, each affixing an anchor member 40 to the bone. Tension members 3 provide the links between 1 and 40. Distraction force 105 is generated by selecting the member 1 and the lengths of the members 3, so that the distance between the tension elements is larger than the distance between the receiving anchors. For installation, the elastic member 1 is compressed by an instrument (for example an adapted forceps) to allow for the conical elements 10 (FIG. 2) to engage into receiving holes of the members 40. If the distraction is maintained long enough to allow for healing of the fracture 106, but without a strong impediment of the other movements in the effected segment of the spinal column, once the device is removed, the column may retain most of its natural range of motion.

Another use of the device according to the present invention is for treating disc pathologies, e.g. extrusion of the disc 107. If the intended treatment is fusion of the spine at this location, the device, deployed as shown, can restrict the range of movement sufficiently for the consolidation of bone graft applied over the affected disc 107.

While the main clinical indications are expected to be for distraction, the same principles can be used to produce compression, by simply machining the receiving holes with the conical holes in the other direction. In fact, it is a simple design and production matter to produce a receiving hole tapered from both ends, which then can be used in either direction.

Having disclosed at least one embodiment of the present invention, various adaptations, modifications, additions, and improvements will be readily apparent to those of ordinary skill in the art. Such adaptations, modifications, additions and improvements are considered part of the invention, which is only limited by the several claims attached hereto.

What is claimed is:

1. An implant for flexible distraction between two anchor points on the skeleton of a human or veterinary patient, the implant comprising a flexible, U-shaped elastic member with two free ends, two anchor members, and two flexible tension members coupling the flexible elastic member to the two anchor members, wherein the two flexible tension members are configured to engage the flexible elastic member at the free ends of the flexible elastic member, and wherein the flexible elastic member straddles the two anchor members and applies a distraction force to the anchor members via the two flexible tension members situated between the flexible elastic member and the two anchor members.

2. The implant of claim 1, wherein the two anchor members are configured in size and shape for attachment to a spine of a human or veterinary patient.

3. The implant of claim 1, wherein the two flexible tension members each comprise a conical coupling element affixed to a flexible cable or bundle of filaments.

4. The implant of claim 3, wherein the flexible cable or bundle of filaments comprises a titanium alloy.

5. The implant of claim 4, wherein the titanium alloy is titanium-aluminium-vanadium, titanium-aluminium-niobium or a super-elastic nickel-titanium.

6. The implant of claim 3, wherein the flexible cable or bundle of filaments comprises high strength polymeric fibers.

7. The implant of claim 6, wherein the high strength polymeric fibers comprise ultra high molecular weight polyethylene.

8. The implant of claim 1, wherein the elastic member comprises a titanium alloy.

9. The implant of claim 8, wherein the titanium alloy is titanium-aluminium-vanadium, titanium-aluminium-niobium or a super-elastic nickel-titanium.

10. The implant of claim 1, further comprising two bone screws for attaching the anchor members to bone.

11. The implant of claim 10, wherein the bone screws are locking bone screws.

12. The implant of claim 1, wherein the flexible elastic member applies a distraction force generated, at least in part, from elasticity of the flexible elastic member when deformed.

13. A method of treating a patient who is suffering from an injury to the spine or a disease that causes damage to a spinal disc, the method comprising affixing the implant of claim 1 to vertebrae in the injured or diseased area of the spine.

14. The method of claim 13, wherein the injury to the spine is a fracture.

15. The method of claim 13, wherein the patient is a human or domesticated animal.

16. An implant for flexible distraction between two anchor points on the skeleton of a human or veterinary patient, the implant comprising a flexible, U-shaped elastic member having first and second terminal regions, an anchor member, and a flexible tension member coupling the flexible elastic member to the anchor member, wherein the flexible tension member is configured to engage the flexible elastic member at the second terminal region, wherein the first terminal region comprises means for attaching the elastic member to a skeletal element and the second terminal region interacts with the anchor member via the flexible tension member, and wherein the flexible elastic member straddles at least the second terminal region.

17. The implant of claim 16, wherein the first terminal region comprises an opening configured to receive a bone anchor, a surface compatible with bone cement, or a feature that can be affixed with a surgical suture.

* * * * *